United States Patent [19]

Theres

[11] Patent Number: 4,971,057
[45] Date of Patent: Nov. 20, 1990

[54] ELECTRICAL CONNECTING MEANS FOR ESTABLISHING MECHANICAL AND ELECTRICAL CONNECTIONS BETWEEN AN IMPLANTABLE MEDICAL DEVICE AND A LEAD SYSTEM

[75] Inventor: Heinz P. Theres, Munich, Fed. Rep. of Germany

[73] Assignee: Dr. Eckhard Alt, Ottobrunn, Fed. Rep. of Germany

[21] Appl. No.: 447,395

[22] Filed: Dec. 7, 1989

[51] Int. Cl.⁵ ............................................. A61N 1/00
[52] U.S. Cl. ............................................. 128/419 P
[58] Field of Search .................. 128/419 P, 784, 785, 128/786; 439/909, 668, 669, 840

[56] References Cited

U.S. PATENT DOCUMENTS

| | | | |
|---|---|---|---|
| 4,278,093 | 7/1981 | Laforturne et al. | 128/419 P |
| 4,469,104 | 9/1984 | Peers-Trevarton | 128/419 P |
| 4,848,346 | 7/1989 | Crawford | 128/419 P |

Primary Examiner—Lee S. Cohen
Assistant Examiner—Scott M. Getzow
Attorney, Agent, or Firm—Laurence R. Brown

[57] ABSTRACT

An implant medical device system with an implant lead system e.g. a heart pacing probe system, connectable thereto provides for at least three implant leads to be connected by a single plug-socket assembly to the medical device system, e.g. a pacemaker. Two contacts on the outside of a connector of this invention form respective electrical contacts with contact areas on a socket made to acceptable medical industry approved structures for bipolar connection systems and feature identical outer diameters. The additional contacts are formed in a way that a pin is mounted in the socket and protrudes into the inner lumen of the connector making additional contacts on the inner side of the central lumen within the connector. Appropriate sealing means ensure the adequate insulation for the additional contacts. The total size of this multicontact connection system stays within the limits of a standard bipolar system, and is interchangable with standard bipolar connection means.

19 Claims, 2 Drawing Sheets

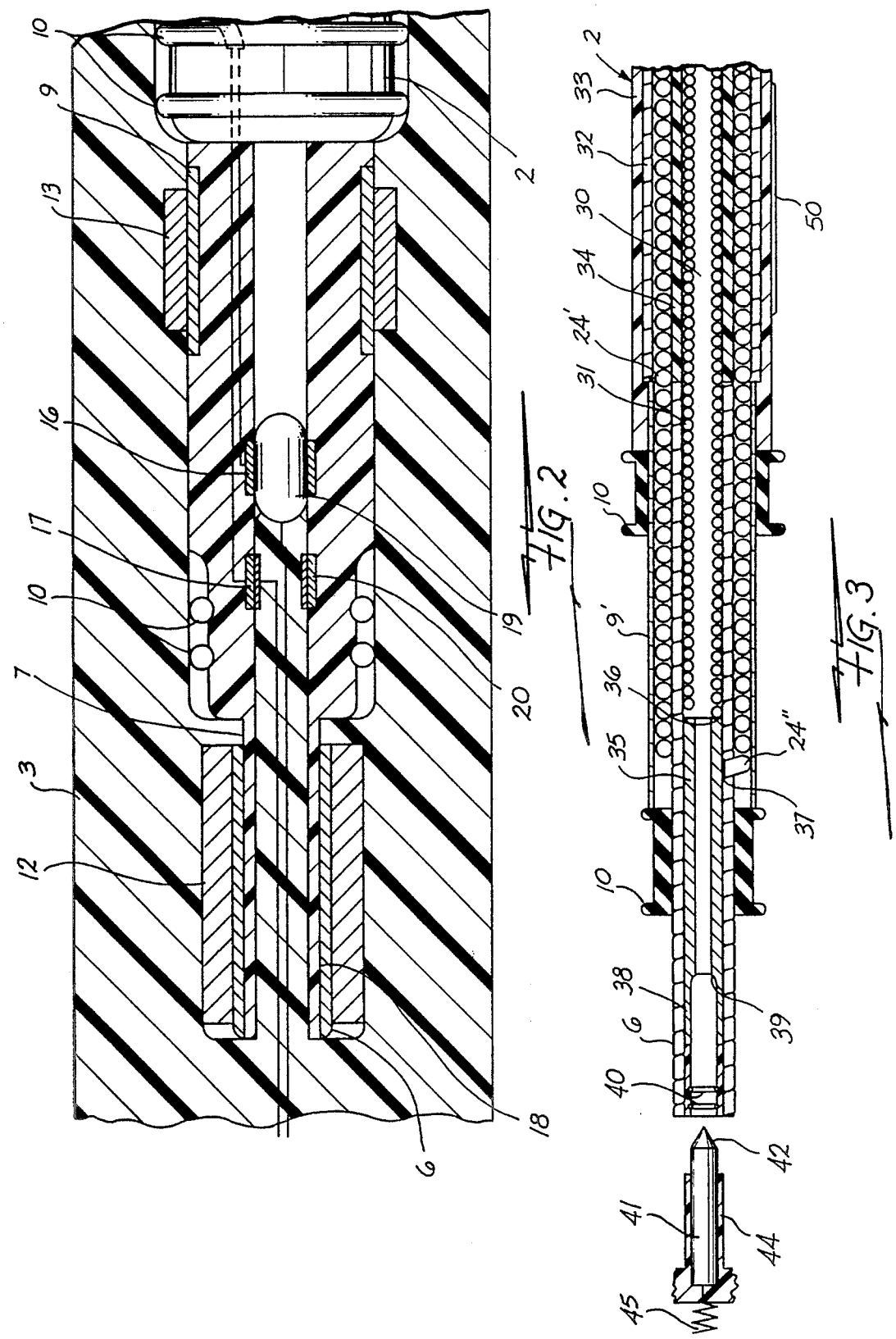

ELECTRICAL CONNECTING MEANS FOR ESTABLISHING MECHANICAL AND ELECTRICAL CONNECTIONS BETWEEN AN IMPLANTABLE MEDICAL DEVICE AND A LEAD SYSTEM

TECHNICAL FIELD

The present invention relates to implantable medical device systems including electrical connecting means comprising a plug and a socket for establishing mechanical and electrical connections between an implantable medical device and lead system.

BACKGROUND ART

Such electrical connecting means are used e.g. for cardiac pacemakers, the implanted pacemaker device being connected to a lead system inserted into the heart, as well as for implantable defibrillators, implantable pumps for metered administration of drugs, e.g. insulin, and devices for stimulating the muscles and nerves.

In the field of implantable cardiac pacemaker technology, considerable change has taken place in recent years. The use of modern microprocessor technology has allowed the systems to become much smaller, on the one hand, and greatly increased their efficiency in processing biomedical signals, on the other hand. The reduction in size of implantable pacemakers made it necessary to reduce the size of the connecting means between the can and the lead system accordingly. Whereas the connecting means between the implantable lead and the pacemaker can had an outside diameter of five or six millimeters in the area of the plug in the early pacemakers this diameter is now in the range of 3.2 millimeters. At the end of 1987 an international convention was worked out with the goal of unifying an electrical connecting means with plug diameters of 3.2 millimeters. On Jan. 27, 1989, such a standard, the so-called IS-1 Standard, was presented in a communication from the IEC/ISO International Pacemaker Standard Working Group IEC SC 62D/WG6 ISO TC 150/SCWG2. This standardized electrical connecting means can be used both for unipolar and for bipolar pacemaker and is now being produced by virtually all manufactures of cardiac pacemakers.

The plug of this electrical connecting means has a front contact pin having a first diameter of slightly less than 1.6 millimeters, an adjacent insulator with sealing elements and a diameter of about 2.6 millimeters, and a following cylindrical contact ring therebehind that is coaxial with the front contact pin and also has a diameter of about 2.6 millimeters. This is followed by another insulator that passes into the lead system and comprises appropriate sealing elements. The contact pin and the contact ring are provided with electrical leads that are run in the lead system and designed e.g. as mutual insulated and banked coils. The socket for the plug has a stepped bore adapted to the diameters of the plug and in which corresponding contact surfaces are provided for the front contact pin and the contact ring.

The use of one connecting means for either unipolar or bipolar pacemaker systems complies in particular with the clinical finding that bipolar pacemaker systems are better protected against interference effects. While polar pacemaker systems involved numerous negative aspects in the past so that unipolar systems were frequently preferred, the disadvantages of bipolar pacemaker systems have now been eliminated so that these systems can now be given preference. A survey on this can be found in the article by E. Alt, "Kritischer Vergleich uni- und bipolarer Schrittmachersysteme," published in Zeitschrift fur Kardiologle 76, 1987, p. 189–194.

Pacemaker systems having a plurality of additional intracardiac or intravascular electrode points have also been proposed in recent years. Within one lead it is thus possible to measure e.g. the atrial potentials in the atrium; cf. D. E. Antonioli et al. in C. Meere, Cardiac pacing PACE Symposium, Montreal 1967. A more precise detection of the atrial potentials with additional electrode points i.e. more than two within a pacing lead inserted into the heart has been described in the past by several authors. These additional electrode points in the heart, whose electrical leads are run within the lead system for the pacing lead, are connected to the pacemaker in such a way that a plurality of separate electrode plugs are connected to the pacemaker can. Pacemaker leads with a plurality of electrode points wherein the electrode leads are bifurcated and connected to a plurality of plugs are also known in the field of cardioversion; cf. U.S. Pat. No. 4,499,907.

With the increasing clinical use of rate adaptive cardiac systems, the implantation of additional sensors in the human organism has acquired growing clinical importance. EP-A No. 10178 528 describes a cardiac pacemaker system in which additional electrodes are used to measure the systolic pressure or its time derivative in the right ventricle. The electrical leads for the electrodes are run within the lead or probe for the pacing electrode and end in a plug received in a socket in the pacemaker can. The electrical contact between the plug and the socket is established via a plurality of contact rings on the plug and corresponding contact surfaces in the socket. This patent also describes the possibility of surrounding a front central contact pin by a plurality of satellite pins which are considerably smaller than said pin. The socket then has additional receiving sockets for these satellite plugs. Such an electrical connecting means can establish electrical contacts necessary for the pacemaker system described therein, but the plug is incompatible with standardized electrical connecting means of the aforesaid type and cannot be built with such small diameter as the currently used bipolar IS-1 Standard connector. A further major drawback is the complicated isolation of all these additional satellite plugs.

In bipolar pacemaker systems equipped with additional sensors, e.g. for measuring the blood temperature or the blood oxygen content, and therefore always requiring more than the two contacts available in the electrical connecting means, the line leading from the pacing lead and the additional sensors is therefore opened so that the lines for the additional sensors end in a separate plug which is introduced into an additional socket in the pacemaker can. The same applies to pacemaker systems having a plurality of sensors for measuring a corresponding plurality of parameters, which are being developed at a forced pace at present; cf. e.g. E. Alt et al., "A new Rate Modulated Pacemaker System—Optimized by Combination of Two Sensors" in PACE Vol. 11, 1119–1129, August 1988.

Defibrillators also require measured values from a plurality of sensors for correctly detecting the indication for defibrillation. Such parameters are not only electrical variables but increasingly also hemodynamic parameters which are detected by appropriate sensors.

Neurostimulators also stimulate not only in the area of one neuromere but in the area of a plurality thereof, so that here, too, a plurality of electrical leads are required which must be connected to a corresponding implant containing a control circuit.

Furthermore, implantable devices are being increasingly used for treating metabolic changes, e.g. diabetes mellitus. In the latter case, the administration of insulin with the aid of an implantable micropump is controlled partly via sensors which are connected by electrical contacts to the implant containing a control circuit and the pump. Here, too, a plurality of leads is required.

Further electrical connecting means having more than two contacts are known from U.S. Pat. Nos. 4,603,696, 4,236,525, 4,527,605, 4,323,081, 4,268,725, 4,411,277, 4,245,642, 4,411,276 and 4,538,623. All these models are special fabrications or improvements which can only be connected to a specially produced implantable medical device. None of these connecting means is compatible with devices obeying the aforesaid standard for electrical connecting means. It is therefore desirable to provide a universally applicable connecting means which is compatible with standardized connecting means. This is of general relevance in those cases, where a lead with more than two contacts and a special sensor is implanted for a given medical indication in a given patient. In the timely course there might be change in the clinical status of the patient and a standard bipolar connection as discussed would be preferable to connect a standard device to the formerly implanted special lead.

A further major concern is the isolation of a third pole. Since it is most likely that any kind of sensor that yields typically very small voltages might be connected, a high degree of isolation such as more than 100 kilo Ohms, preferably even more than 0.5 Megohm Ohm, is mandatory for correct function. In order to achieve an isolation of this order, improved sealing means are needed. Since implantable devices are getting smaller and smaller, bulky insulation on the outside of a connector increases the size of the whole connecting means intolerably.

It is therefore a major aim of this invention to provide excellent sealing means for a third connection without increasing the size of a connection system over the size that is used with the aforediscussed standard. Conventional kinds of contact and sealing structure on the outside of a connector cannot solve the aforementioned requirements. The present invention givens a solution to those requirements.

BRIEF DESCRIPTION OF THE INVENTION

The invention is therefore based on the problem of creating electrical connecting means of the type in question which deviates only slightly from the known standardized connecting means but is compatible therewith and furthermore has more than the two contacts available up to now.

This problem is solved according to the invention by the features set forth throughout the following specification, claims and drawings.

Accordingly, a multiple contact connector is provided which is mechanically replaceable with the aforesaid standardized connector means, which has an insulator disposed between a front contact pin and a trailing contact ring. One or more additional contacts are disposed on the inner bore of the front contact pin of a plug so as to cooperate with additional mating contacts in the socket that fit into the bore of the inside of the front contact pin. The outer dimensions of the plug and the inner dimensions of the socket are adapted to the above-mentioned IS-2 Standard, so that both the plug and the socket are compatible with standardized connecting means while making additional contacts available. A simple possibility is provided for disposing the additional contacts within the plug and the additional opposite contacts on the socket when a standardized plug with the adjacent probe leading to an individual electrode has a lumen for receiving a stilette or mandrin, i.e. a guide wire for introducing the probe reliably into the human vascular system and placing it there. After implantation the guide wire is then removed so that the probe has a free inside lumen.

It is therefore possible to disposed at least one contact ring insulated from the standard connector pin and flush with the wall of this inside lumen in the area of an insulator within a cavity through the standard plug length. A corresponding contact pin, extending from the socket and coaxially mounted within the ring contact for the plug pin, engages the region inside the plug with at least one opposite contact that electrically contacts the additional contact ring within the plug.

A solution for the aforementioned problem of additional contacts could be to provide the outer wall of the plug with at least one other additional contact ring in the area within the plug insulator, which cooperates with corresponding electrical contact means on the inner wall of the contact pin extending from the socket. In such an embodiment, however, relatively little space is available for the additional contact rings on the plug since about half the insulator length is required for mechanical contact elements, e.g. sealing rings, to ensure a reliable and electrically insulated seat of the plug in the socket. For disposing additional contacts within the lumen of the plug, on the other hand, the entire length of the insulator can be used and this invention provides excellent sealing facilities without increasing the outer diameter. This is extremely important since with time, always some moisture gets into the inner side of the socket which is mainly built from epoxy resin.

The inventive connecting means provides additional electrical contacts while having the same dimensions as standardized connecting means, so that an implantable medical device, e.g. a cardiac pacemaker, can also be equipped with additional sensors without any change in the dimensions of the connecting means. The connecting means can be provided with multiple contacts and a corresponding plurality of electrode conductors which are of coaxial type construction. Electrode conductors can also be used which comprise a plurality of individual, mutually insulated wires which are bound parallel next to each other. One can also use electrode conductors having a plurality of individual, mutually insulated conductors with a central coil coaxial conductor and satellite conductors disposed peripherally therewith and embedded in a common insulating compound.

Connecting means according to the invention can be used for converting implanted lead systems of three or more conductors with a single standard dimension connector mounted on corresponding cardiac pacemakers, defibrillators, neurostimulators, infusion pumps and other implantable medical devices.

In order to facilitate the identification of the visually difficult to identify multicontact lead connector it is suggested that a labeling like IS-1-TRI or QUATRO and an additional identification like temperature, pressure, oxygen, or so on, might be disposed on the insulation body by a legend 50 in order to facilitate identification for the following physician in the case of reoperation.

Other embodiments of the invention can be found within the scope of the invention as set forth in the appended claims.

BRIEF DESCRIPTION OF THE DRAWINGS

The invention is described in more detail in exemplary embodiments with reference to the drawing, in which

FIG. 2 shows a detail of FIG. 1;

FIG. 3 shows diagrammatically in cross section, a preferred embodiment of the invention.

THE PREFERRED EMBODIMENTS

Figure 1:
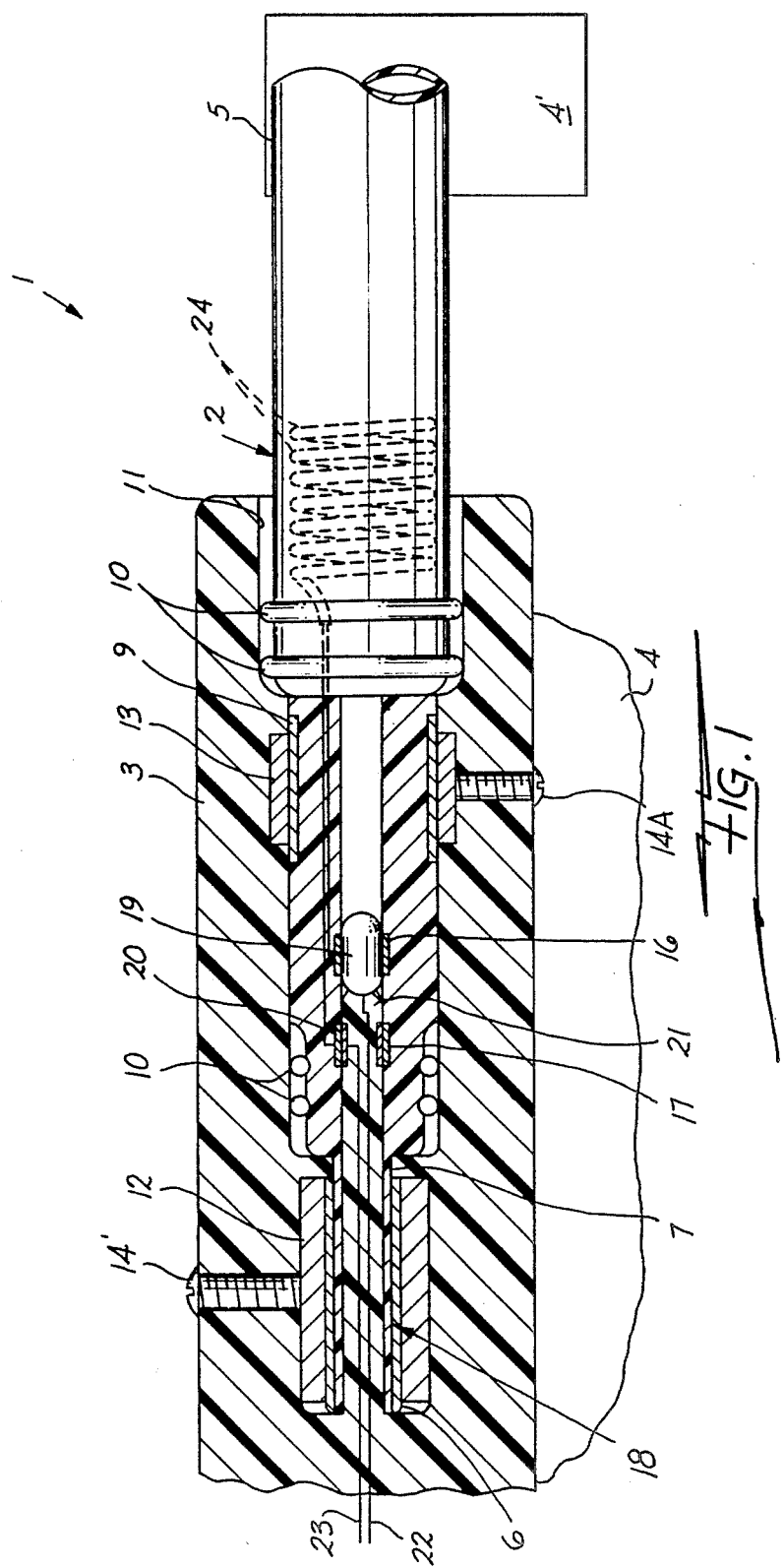
FIG. 1 shows a longitudinal section of an electrical connecting means according to the invention.

FIG. 1 shows electrical connecting means 1 comprising a plug 2 and a socket 3. An implantable medical device 4, such as an implanted pacemaker coupled to an implanted lead system 11 via socket 3 is, for example, part of a can 4 of a cardiac pacemaker. Plug 2 passes into a lead or a probe 5 which leads to a lead system 4' comprising e.g. a pacing electrode and at least one further measuring electrode.

Plug 2, preferably with the standard dimensions (IS-1) above identified, has a front contact pin 6 having a first diameter and a contact zone 7, an adjacent insulator 8 having a second, greater diameter and a following contact are having a contact ring 9 whose outside diameter corresponds to that of insulator 8. This contact area then passes into probe 5 whose diameter exceeds that of contact ring 9. In the area of insulator 8 facing front contact pin 6 there are two sealing rings 10 made, for example, of silicon rubber in order to insulate the connector towards the outer ends at the plug shoulders. Such rings are also provided in the foremost area of lead 2 distal to contact ring 9 towards distal contact pin 6, insulating pin 6 and ring 9.

Socket 3 has stepped bore 11 whose diameter is adapted to those of the contact pin 6, the insulator 8 and the plug 2. In stepped bore 11 there are annular contact surfaces 12 and 13 which lie against contact zone 7 of front contact pin 6 and against second contact ring 9, respectively. These contact surfaces 12 and 13 can be pressed with the aid of screws 14 and 14a against contact zone 7 and contact ring 9 to ensure a good electrical connection. Alternatively, screws 14 and 14a can also establish the electrical and mechanical contact alone, without contact surfaces 12 and 13.

Plug 2 and lead 5 have a longitudinal inner lumen 15. In the area of insulator 8 two contact surfaces 16 and 17 are additionally provided flush with the inner wall of lumen 15 in the form of contact rings or sets or spring clip contact. From socket 3 a contact pin 18 protrudes into lumen 15, said pin bearing two mating contacts 19 and 20 which lie against contacts 16 and 17, respectively. Mating contact 19 forms the tip of the contact pin 18 and is separate from annular second opposite contact 20 by insulation 21. Insulation ring 21' insulates contact 20 and contact area 17 from the outside of the inner longitudinal lumen 15a. Leads 22 and 23 are run in the conventional manner inside contact pin 18 for mating contacts 19 and 20. The design of such contact pins is well within the skill of the art as is well known from so-called jack plugs.

The leads for contact surfaces 12 and 13 on the socket side, which are not shown in FIG. 1, are designed in the conventional manner as in the aforesaid standard. The same applies to contact zone 7 and contact ring 9. The electrical leads are run within probe 5, e.g. in the form of mutually insulated and banked coils 24 as indicated in probe 5. The electrical leads for additional opposite contacts 19 and 20 can also be included here, so that coil 24 comprises four mutually insulated lines. Other arrangements are of course also possible, e.g. a superposed or even a linear arrangement of conductors within probe 5.

FIG. 3, diagrammatically shows in cross section a preferred embodiment that can conform to the aforesaid standards. Thus an inner lumen 30, defined by the coiled wire spiral 31 has a diameter of 0.45 mm in order to permit easy passage of a 0.35 mm diameter stylet. The wires as that of the outer coil spirals 24' and parallel wires 24'' are insulated by a wire coating. The outer spiral 24' is covered by the spiral metal tubing 32, and insulation layer 33. The tubing 32 is continued at reduced diameter outside the rubber sealing ring 10 to form the outer connector surface 9' of the plug assembly 2. Coil 24' forms an electrical contact to tubing 32 in such a way that part of the surface insulation is removed in the area of contact 9' coil from 24'.

Between the outer wire coil spiral 24 and the inner wire coil spiral 31 is an insulation layer 34, which ends at the beginning of the metallic connector tubing 6. Coil spiral 31 electrically connected to distal pin 6.

An inner connector comprises the cylindrical tubing 35 which abuts and is electrically insulated at 36 to the inner wire coil spiral 31. One of the metal tube outer wire coil spirals 24', namely 24'' is connected to the inner 35 at 37. A respective bore in tube 6 allows passage of the coated wire 24' which is affixed to metal tube 35 by laser welding. Metal tube 6 and inner tube 35 are insulated from each other. The cylindrical tubing 35 has an inner diameter of 0.45 mm conforming with the lumen diameter, but at its outer end 38 has a larger diameter to provide a conical surface 39 for engagement with metal pin 41 at conical end 42 as the inner connector. The silicon rubber outside seal 40 will insulate the pin from the connector 6 and from the outside of the socket bore 11. An insulating coating on inner surface of connector pin 6 prevents electrical contact with the cylinder 35. This insulator 40 also serves as a moisture seal.

Further the spring loaded pin 41 carries an outer insulation coating 44. The pin 41 has at its end appropriately mounted in the socket assembly (not shown) a spring 45 for urging the pin connector into the cylindrical member 35 for contact on the respective conical surfaces 39, 42.

It is clear therefore that this embodiment provides a flexible catheter meeting the industry standards and providing for more than two connecting wires whereby the third contact that normally connects a sensor line is situated and tightly sealed within the distal contact pin.

I claim:

1. An implanted medical system with improved connecting means disposed between an implanted medical device and implanted leads for connecting more than two conductors to the medical device with a single plug-socket assembly, comprising in combination, a basic plug member with an inner lumen along its length having a substantially cylindrical contact pin of small diameter surrounded concentrically at one end by an insulating member of greater diameter, and a further contact member substantially concentrically positioned about the contact pin to abut said insulating member longitudinally, and probe means for coupling two implanted conductors to the contact pin and further contact member respectively, a basic socket member with mating cavities disposed substantially concentrically about the plug member contact pin, insulating member and further contact member with mating contact means for coupling two conductors in the medical device thereto respectively, and at least one additional contact member disposed along the length of the inner lumen in said plug member and insulated from the contact pin and further contact member with a corresponding mating contact member in said socket member for connecting a further implanted conductor through the additional contact member and mating contact member to a conductor in the medical device.

2. The system of claim 1 further comprising a plug having three longitudinally disposed generally cylindrical sections of different diameters contiguously positioned end to end and a socket with mating cylindrical receptacle cavities for receiving the plug section in a registered position with the three contact members of the plug and socket registered in contact.

3. The system of claim 1 further comprising said contact pin of a diameter of substantially 1.5 mm.

4. The system of claim 1 further comprising said insulating member with a diameter of substantially 2.6 mm.

5. The system of claim 1 further comprising at least one sealing ring disposed about said connecting means for mating in sealed position within one said socket cavity when the contact members are mated.

6. The system of claim 1 further comprising at least one sealing ring disposed about said inner lumen of the distal contact pin on the plug for mating in sealed position when the contact members are mated.

7. The system of claim 1 wherein a body on the plug extends from the connecting means further comprising identification means on the plug body in order to facilitate identification of specification of the connecting means and the additional contact member.

8. The system of claim 1 further comprising identification means on the implantable medical device in order to facilitate identification of specifications of the connecting means and the additional contact member.

9. On a implanted medical system comprising in combination, a plus and a socket forming connecting means disposed between an implanted medical device and implanted leads for connecting more than two electrical lines, the improvement comprising both male and female contacts on both the plug and on the socket.

10. An implanted medical system with improved connecting means disposed between an implanted medical device and implanted leads for connecting more than two conductors to the medical device with a single connector plug-socket assembly namely, a plug and a socket, having a bipolar connection meeting established standard dimensions for connectors approved for the medical field, with a male contact member of the connector assembly formed by a distal pin and a more proximal ring contact member that engage with female contact areas in a socket region, the improvement comprising at least one additional contact member on the inside of an inner lumen of the connector assembly and a contact pin that is mounted inside the socket region and protrudes into the inner lumen of the connector assembly thereby forming an additional electrical contact connection.

11. The system defined in claim 10 further comprising a fourth contact member disposed along the length of the inner lumen in said plug and a fourth contact member in the socket for mating therewith for connecting a fourth implanted conductor to a corresponding conductor in the medical device.

12. The system of claim 4 further comprising an inner lumen in the connector assembly with the disposition of the one additional and fourth contact members on said plug concentrically inside an insulating member of the inner lumen.

13. The system of claim 10 further comprising said two implanted conductors extending from the connecting means comprising at least one generally cylindrically disposed conductor, a lumen passing through the plug and coaxially within the cylindrically implanted conductors extending from said connecting means, and wherein the additional contact member is disposed on an inner surface of said lumen.

14. An implant medical device and implant lead system therefor connectable by means of a single plug and socket, comprising in combination, three implant leads in said lead system terminating in a plug having two contacts members on an outside surface of the plug, connected to respective ones of the implant leads wherein one contact member comprises a cylindrical pin of about 1.5 mm diameter, and another contact member comprises a substantially cylindrical member of about 2.6 mm diameter, having a third contact member on an inside lumen surface of the plug, a socket mounted on said medical device with cavities and mating contact members for receiving said plug to connect the three leads through the respective mating contact members to three conductors in the medical device.

15. The system of claim 14 wherein said connecting means comprises an electrode catheter having an inner lumen extending from the lumen surface of the plug, and wherein said third contact member located within the inside lumen surface of the plug further comprises a cylindrical connector members forming part of said lumen surface adapted to receive a mating connecting member carried by the socket member therein.

16. The system of claim 15 wherein the inside lumen surface of the plug has a diameter in the order of 0.45 mm.

17. The system of claim 15 further comprising conically interengaging surfaces on said cylindrical connector member forming part of said lumen and the mating connector surfaces.

18. The system of claim 15 wherein said mating connecting member further comprises spring means in the socket member biasing the mating connecting member toward said cylindrical connecting member forming part of said lumen surface.

19. The system of claim 15 further comprising insulation moisture sealing means about said mating connecting member for sealing an end of said lumen when the cylindrical connector member and mating connector of the additional contact member are in engagement.

* * * * *

UNITED STATES PATENT AND TRADEMARK OFFICE
CERTIFICATE OF CORRECTION

PATENT NO. : 4,971,057

DATED : November 20, 1990

INVENTOR(S) : Heinz Theres

It is certified that error appears in the above-identified patent and that said Letters Patent is hereby corrected as shown below:

Claim 9, line 1, change "On" to --In an-- line 2, change "plus" to --plug--.

On the title page Insert:

-- Foreign Application Priority data

May 3, 1989 [DE] Fed. Rep. of Germany   P 39 14 677.4 --

Signed and Sealed this

Eighteenth Day of August, 1992

*Attest:*

DOUGLAS B. COMER

*Attesting Officer*   Acting Commissioner of Patents and Trademarks